March 22, 1932. C. W. HJERMIND ET AL Plant Pat. 11
HYBRID TEA ROSE
Filed Feb. 28, 1931
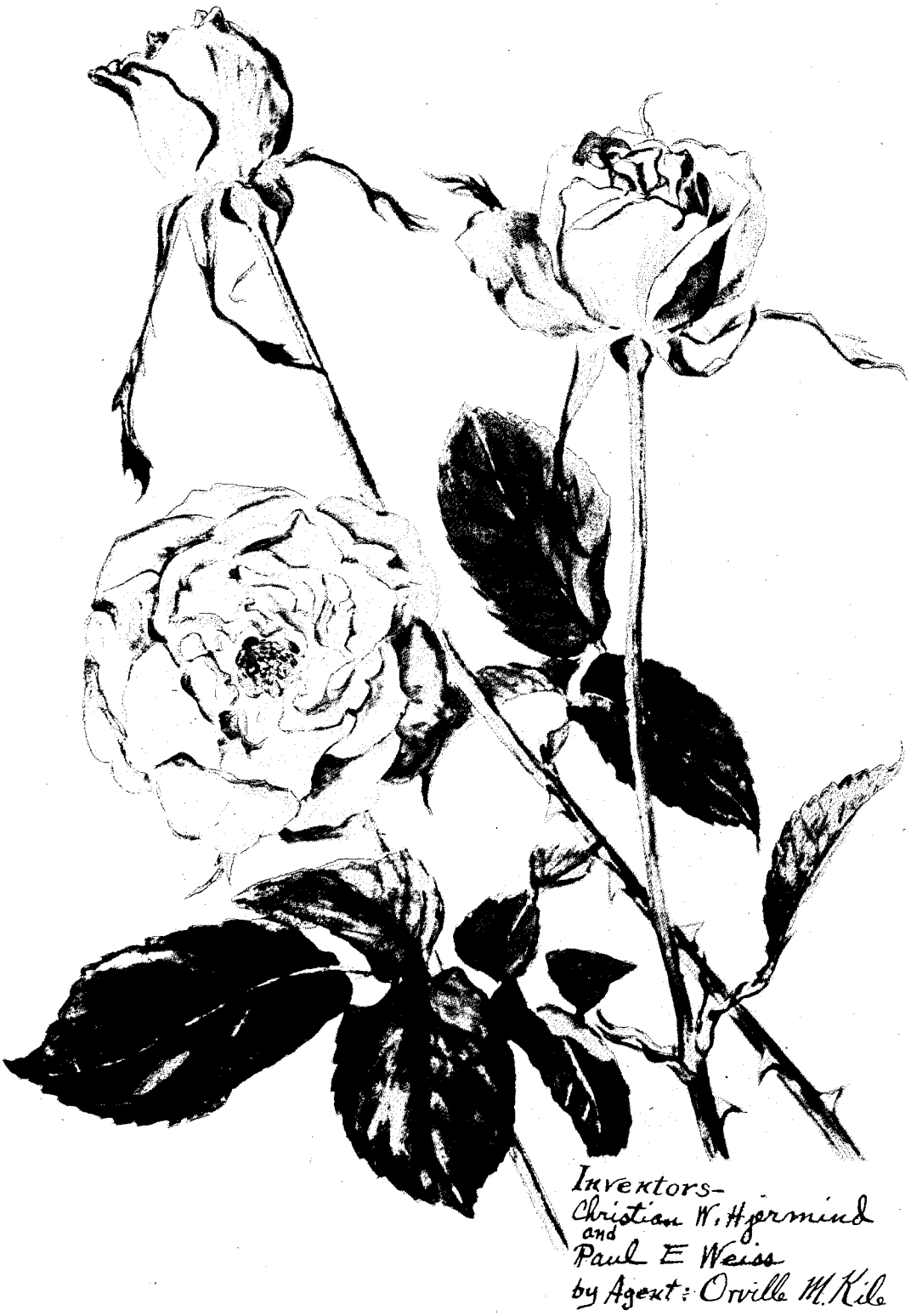

Patented Mar. 22, 1932

UNITED STATES PATENT OFFICE

CHRISTIAN W. HJERMIND, OF MAYWOOD, AND PAUL E. WEISS, OF RIVER FOREST, ILLINOIS, ASSIGNORS TO PREMIER ROSE GARDENS, CONSOLIDATED, OF MAYWOOD, ILLINOIS, A CORPORATION

HYBRID TEA ROSE

Application filed February 28, 1931. Serial No. 519,197.

Our invention relates to improvements in pinkish-red, fragrant, semi-double, hybrid tea roses. The object is to provide a rose of the type mentioned having a deeper and more appealing color, heavier and darker foliage, a better producer and other superior qualities as compared with somewhat similar varieties.

This new rose was first discovered as a sport by the first named of the joint inventors, during the year 1929. The second named joint inventor fostered and developed the plant, studied its characteristics and asexually reproduced it by budding.

The accompanying illustrations show in full color and in approximately natural size, two partly opened buds and a fully opened flower of our new variety. The color shown is that of flowers cut 36 to 40 hours but carefully wrapped, moistened and boxed, for all but the last 8 hours of this period. When growing or fresh cut the coloring is much lighter—a dark pink with lighter shades on the insides of the petals. In fact the decided change in color after cutting is an important character of this new rose.

The following is a detailed description of this rose:

A bush or upright rose, of vigorous growth, and free blooming habit. Stem substoutish, green, beset with average number of stoutish, greenish, beak-shaped spines or prickles, retrorsely directed, nearly straight on upper surface; the peduncle, or upper stem bearing the flower, straightish to moderately sinuous.

Leaves, on flower-bearing stem, 4 to 6 inches long, glabrous, the petioles glabrous or bearing a few glandular hairs; the leaflets 3 to 5 (on second to fifth leaves), ovate, serrate or crenate-serrate with short teeth, acute or abruptly short-acuminate, deep green.

Stipules subfoliaceous, veiny, becoming leaf-green, 3/4 to 7/8 inch long including tips, the pair 3/8 to 7/16 inch wide, adnate to petiole for about 5/8 inch, finely serrulate with short gland-tipped teeth, the long-acuminate tip about 3/16 to 1/4 inch long.

Hips in the bud and opening flower about 1/2 inch long and 1/2 inch wide, broadly oboval, abruptly narrowed to peduncle.

Buds at opening about 1 1/2 inches long, excluding hips; stoutish.

Sepals usually 5, about 1 1/2 to 2 1/2 inches long including tips, in the opening flowers, long-acuminate from a narrowly lanceolate base, the margins more or less beset with short, glandular hairs and bearing occasional long subulate teeth, densely soft-pubescent inside (above), glabrous outside (beneath); the sepal tip in the opening bud developing into a more or less leaflike appendage, narrowly lanceolate or oblandeolate, 1/2 to 1 1/2 inches long, the larger toothed on the margins.

Flowers borne singly on long stems, mid-sized, 3 1/2 to 4 inches wide when fully open, very fragrant, semi-double.

Petals, 23 to 25, broadly obovate to suborbicular, often somewhat apiculate, veins numerous, prominent, reticulate; color, pinkish changing to rose red and even to pomegranate purple (of the Ridgway color scale) upon being cut and exposed to the air with the stems in water. The petals are moderately to deeply flushed with orange yellow. The illustrations show the color under these latter conditions.

We claim:

The hybrid tea rose herein shown and described, chiefly characterized by its rose red color, flushed with orange yellow, semi-double petalage, foliaceous sepals, heavy dark green foliage, and superior producing qualities.

C. W. HJERMIND.
PAUL E. WEISS.